US012806248B2

(12) United States Patent
Huang et al.

(10) Patent No.: US 12,806,248 B2
(45) Date of Patent: Nov. 24, 2026

(54) INCRETIN ANALOGUE, PREPARATION METHOD THEREFOR, AND USE THEREOF

(71) Applicants: ZHEJIANG DOER BIOLOGICS CO., LTD., Hangzhou (CN); ZHEJIANG HEZE PHARMACEUTICAL TECHNOLOGY CO., LTD., Hangzhou (CN)

(72) Inventors: Yanshan Huang, Hangzhou (CN); Yonglu Chen, Hangzhou (CN); Wenwen Duan, Hangzhou (CN); Xiaofang Wen, Hangzhou (CN); Yuanyuan Liu, Hangzhou (CN); Yuan Wang, Hangzhou (CN); Shimei Sheng, Hangzhou (CN); Ying Liu, Hangzhou (CN); Sheng Ni, Hangzhou (CN); Mingyue Zhu, Hangzhou (CN); Chen Fang, Hangzhou (CN); Peng Sun, Hangzhou (CN)

(73) Assignees: ZHEJIANG DOER BIOLOGICS CO., LTD., Hangzhou (CN); ZHEJIANG HEZE PHARMACEUTICAL TECHNOLOGY CO., LTD., Hangzhou (CN)

( * ) Notice: Subject to any disclaimer, the term of this patent is extended or adjusted under 35 U.S.C. 154(b) by 1019 days.

(21) Appl. No.: 17/916,169

(22) PCT Filed: Feb. 26, 2021

(86) PCT No.: PCT/CN2021/078194
§ 371 (c)(1),
(2) Date: Sep. 30, 2022

(87) PCT Pub. No.: WO2021/203864
PCT Pub. Date: Oct. 14, 2021

(65) Prior Publication Data

US 2023/0218721 A1 Jul. 13, 2023

(30) Foreign Application Priority Data

Apr. 8, 2020 (CN) ........................ 202010269596.0

(51) Int. Cl.

| | |
|---|---|
| *A61K 38/22* | (2006.01) |
| *A23L 33/10* | (2016.01) |
| *A23L 33/18* | (2016.01) |
| *A61K 38/00* | (2006.01) |
| *A61K 47/54* | (2017.01) |
| *A61P 1/16* | (2006.01) |
| *A61P 3/04* | (2006.01) |
| *A61P 3/06* | (2006.01) |
| *A61P 3/10* | (2006.01) |
| *A61P 5/50* | (2006.01) |
| *C07K 14/605* | (2006.01) |

(52) U.S. Cl.
CPC ............ *A61K 38/22* (2013.01); *A61K 47/542* (2017.08); *A61P 3/04* (2018.01); *A61P 3/10* (2018.01)

(58) Field of Classification Search
CPC ...... A61K 38/00; A61K 38/22; A61K 47/542; A61P 1/16; A61P 3/04; A61P 3/06; A61P 3/10; A61P 5/50; C07K 14/605; A23L 33/10; A23L 33/18
See application file for complete search history.

(56) References Cited

U.S. PATENT DOCUMENTS

2015/0368310 A1* 12/2015 Dimarchi .................. A61P 3/04 530/308
2022/0340635 A1* 10/2022 Huang .................. C12N 15/62

FOREIGN PATENT DOCUMENTS

| | | | |
|---|---|---|---|
| CN | 107207576 | A | 9/2017 |
| CN | 109776670 | A | 5/2019 |
| CN | 109836488 | A | 6/2019 |
| CN | 109836503 | A | 6/2019 |

OTHER PUBLICATIONS

CN 107207576 English translation from Google Patents, Sep. 26, 2017, pp. 1-55. (Year: 2017).*
Type 1 Diabetes from CDC (https://www.cdc.gov/diabetes/about/about-type-1-diabetes.html), pp. 1-3. Accessed Nov. 2025. (Year: 2025).*

* cited by examiner

*Primary Examiner* — Julie Ha
(74) *Attorney, Agent, or Firm* — IPRTOP LLC

(57) ABSTRACT

Provided is an incretin analogue, a preparation method therefor, and the use thereof. The incretin analogue has a GLP-1R/GIPR/GCGR agonist activity, is a triple agonist, and can be used for lowering blood glucose, reducing fat and reducing weight.

20 Claims, 4 Drawing Sheets

Specification includes a Sequence Listing.

Cumulative food intake in DIO mice

Fasting blood glucose in DIO mice

SEQUENCE LISTING

```
<160> NUMBER OF SEQ ID NOS: 8

<210> SEQ ID NO 1
<211> LENGTH: 29
<212> TYPE: PRT
<213> ORGANISM: Artificial Sequence
<220> FEATURE:
<223> OTHER INFORMATION: Glucagon
<220> FEATURE:
<221> NAME/KEY: PEPTIDE
<222> LOCATION: (1)..(29)
<223> OTHER INFORMATION: Glucagon

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25


<210> SEQ ID NO 2
<211> LENGTH: 39
<212> TYPE: PRT
<213> ORGANISM: Artificial Sequence
<220> FEATURE:
<223> OTHER INFORMATION: Glucagon-like polypeptide
<220> FEATURE:
<221> NAME/KEY: PEPTIDE
<222> LOCATION: (1)..(39)
<223> OTHER INFORMATION: Glucagon-like polypeptide
<220> FEATURE:
<221> NAME/KEY: MISC_FEATURE
<222> LOCATION: (10)..(10)
<223> OTHER INFORMATION: Xaa at position 10 is Lys
<220> FEATURE:
<221> NAME/KEY: BINDING
<222> LOCATION: (39)..(39)
<223> OTHER INFORMATION: OH or NH2 modification

<400> SEQUENCE: 2

Tyr Ser Glu Gly Thr Phe Thr Ser Asp Xaa Ser Lys Tyr Leu Asp Ser
```

-continued

```
1               5                   10                  15

Gln Ala Ala Gln Asp Phe Val Gln Trp Leu Leu Ala Gly Gly Pro Ser
            20                  25                  30

Ser Gly Ala Pro Pro Pro Ser
        35
```

<210> SEQ ID NO 3
<211> LENGTH: 31
<212> TYPE: PRT
<213> ORGANISM: Artificial Sequence
<220> FEATURE:
<223> OTHER INFORMATION: GLP-1
<220> FEATURE:
<221> NAME/KEY: PEPTIDE
<222> LOCATION: (1)..(31)
<223> OTHER INFORMATION: GLP-1

<400> SEQUENCE: 3

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 4
<211> LENGTH: 42
<212> TYPE: PRT
<213> ORGANISM: Artificial Sequence
<220> FEATURE:
<223> OTHER INFORMATION: GIP
<220> FEATURE:
<221> NAME/KEY: PEPTIDE
<222> LOCATION: (1)..(42)
<223> OTHER INFORMATION: GIP

<400> SEQUENCE: 4

```
Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40
```

<210> SEQ ID NO 5
<211> LENGTH: 39
<212> TYPE: PRT
<213> ORGANISM: Artificial Sequence
<220> FEATURE:
<223> OTHER INFORMATION: YELAN
<220> FEATURE:
<221> NAME/KEY: PEPTIDE
<222> LOCATION: (1)..(39)
<223> OTHER INFORMATION: YELAN
<220> FEATURE:
<221> NAME/KEY: BINDING
<222> LOCATION: (39)..(39)
<223> OTHER INFORMATION: OH modification

<400> SEQUENCE: 5

```
Tyr Ser Glu Gly Thr Phe Thr Ser Asp Tyr Ser Lys Tyr Leu Asp Ser
1               5                   10                  15

Gln Ala Ala Gln Asp Phe Val Gln Trp Leu Leu Ala Gly Gly Pro Ser
            20                  25                  30

Ser Gly Ala Pro Pro Pro Ser
        35
```

```
<210> SEQ ID NO 6
<211> LENGTH: 39
<212> TYPE: PRT
<213> ORGANISM: Artificial Sequence
<220> FEATURE:
<223> OTHER INFORMATION: P3YELAN
<220> FEATURE:
<221> NAME/KEY: PEPTIDE
<222> LOCATION: (1)..(39)
<223> OTHER INFORMATION: P3YELAN
<220> FEATURE:
<221> NAME/KEY: MISC_FEATURE
<222> LOCATION: (10)..(10)
<223> OTHER INFORMATION: Xaa at position 10 is K (Palmitoyl- gammaE)
<220> FEATURE:
<221> NAME/KEY: BINDING
<222> LOCATION: (39)..(39)
<223> OTHER INFORMATION: NH2 modification

<400> SEQUENCE: 6

Tyr Ser Glu Gly Thr Phe Thr Ser Asp Xaa Ser Lys Tyr Leu Asp Ser
1               5                   10                  15

Gln Ala Ala Gln Asp Phe Val Gln Trp Leu Leu Ala Gly Gly Pro Ser
            20                  25                  30

Ser Gly Ala Pro Pro Pro Ser
        35


<210> SEQ ID NO 7
<211> LENGTH: 39
<212> TYPE: PRT
<213> ORGANISM: Artificial Sequence
<220> FEATURE:
<223> OTHER INFORMATION: P5YELAN
<220> FEATURE:
<221> NAME/KEY: PEPTIDE
<222> LOCATION: (1)..(39)
<223> OTHER INFORMATION: P5YELAN
<220> FEATURE:
<221> NAME/KEY: MISC_FEATURE
<222> LOCATION: (10)..(10)
<223> OTHER INFORMATION: Xaa at position 10 is K (((octadecanedioic acid
      monoacyl)- gammaE)-2xOEG)
<220> FEATURE:
<221> NAME/KEY: BINDING
<222> LOCATION: (39)..(39)
<223> OTHER INFORMATION: NH2 modification

<400> SEQUENCE: 7

Tyr Ser Glu Gly Thr Phe Thr Ser Asp Xaa Ser Lys Tyr Leu Asp Ser
1               5                   10                  15

Gln Ala Ala Gln Asp Phe Val Gln Trp Leu Leu Ala Gly Gly Pro Ser
            20                  25                  30

Ser Gly Ala Pro Pro Pro Ser
        35


<210> SEQ ID NO 8
<211> LENGTH: 39
<212> TYPE: PRT
<213> ORGANISM: Artificial Sequence
<220> FEATURE:
<223> OTHER INFORMATION: P9YELAN
<220> FEATURE:
<221> NAME/KEY: PEPTIDE
<222> LOCATION: (1)..(39)
<223> OTHER INFORMATION: P9YELAN
<220> FEATURE:
<221> NAME/KEY: MISC_FEATURE
<222> LOCATION: (10)..(10)
<223> OTHER INFORMATION: Xaa at position 10 is K (((eicosandioic acid
      monoacyl)- gammaE)-2xOEG)
<220> FEATURE:
```

-continued

```
<221> NAME/KEY: BINDING
<222> LOCATION: (39)..(39)
<223> OTHER INFORMATION: NH2 modification

<400> SEQUENCE: 8

Tyr Ser Glu Gly Thr Phe Thr Ser Asp Xaa Ser Lys Tyr Leu Asp Ser
1               5                   10                  15

Gln Ala Ala Gln Asp Phe Val Gln Trp Leu Leu Ala Gly Gly Pro Ser
            20                  25                  30

Ser Gly Ala Pro Pro Pro Ser
        35
```

INCRETIN ANALOGUE, PREPARATION METHOD THEREFOR, AND USE THEREOF

CROSS REFERENCE TO RELATED PATENT APPLICATION

The present application is the US national stage of PCT/CN2021/078194 filed on 2021 Feb. 26, which claims the priority of the Chinese patent application No. 202010269596.0 filed on 2020 Apr. 8, which application is incorporated herein by reference.

TECHNICAL FIELD

The present disclosure relates to the field of biotechnology, more specifically, the present disclosure relates to an incretin analogue and a preparation method therefor and a use thereof.

BACKGROUND

Hyperglycemia is caused by defective insulin secretion or its impaired biological action, or caused by both. In clinic, diabetes is generally divided into type 1 diabetes, type 2 diabetes, etc. In diabetes, chronic symptoms of hyperglycemia can lead to chronic damage and dysfunction of various tissues, especially the eyes, kidneys, heart, blood vessels, and nerves, thus threatening human health. In particular, along with the change of lifestyle and the increase of population aging, diabetes and its complications are increasingly becoming an important threat to human health.

The main categories of drugs used in clinical treatment of type 2 diabetes in the prior art include: biguanide diabetes drugs (Metformin, or Phenformin), sulfonylurea diabetes drugs (Glibenclamide, Glipizide, Gliclazide, Glibornuride, Glimepiride, or Gliquidone), glucosidase inhibitor drugs (Acarbose, Voglibose, or Miglitol), insulin sensitizing drugs (Ciglitazone, Troglitazone, Rosiglitazone, or Pioglitazone), aldose reductase inhibitor drugs (Alrestatin, Epalrestat, Bolastat, or Tolrestat), insulinotropic drugs (Repaglinide, or Nateglinide). Although a variety of drugs for the treatment of diabetes have been developed, there are also many negative factors restricting the application of some drugs.

Among the currently marketed protein drugs, those used for treating type 2 diabetes are mainly human glucagon-like peptide-1 receptor (GLP-1R) agonists, such as Liraglutide (Trade names SAXENDA® and VICTOZA®), Semeglutide (Trade name OZEMPIC®), etc. Liraglutide is a chemically-modified GLP-1 analogue, obtained by conjugating a fatty acid (hexadecanoic acid) to lysine at position 26 on the skeleton of GLP-1 protein through gamma-Glu, in which the fatty acid can bind to serum albumin, and the drug can be administered once a day clinically, respectively for the treatment of two indications, i.e. type 2 diabetes mellitus and obesity. In terms of the structure, Semeglutide is a GLP-1 (7-37) chain where Ala at position 8 is replaced by Aib, Lys at position 34 is replaced by Arg, and Lys at position 26 is conjugated to an octadecane fatty acid chain. Compared with Liraglutide, Semeglutide has a longer fatty acid chain, with higher affinity for serum albumin, and it is injected subcutaneously once a week clinically.

Patients with diabetes are generally obese, and weight loss is associated with significant improvement in diabetes. Therefore, with regard to GLP-1 analogues, weight loss is an important indicator. Although Liraglutide has been approved for the treatment of obesity, the actual weight loss is only about 5.6 kg. In contrast, the average clinical weight loss in Semeglutide (0.5 mg) and Semeglutide (1.0 mg) treatment groups is 4.2 kg and 5.5 kg. At present, the weight loss of drugs used for obesity is generally about 5-10% (compared with a placebo), that is, the proportion of the overall average weight loss does not exceed 10% of the patient's body weight (Rudolph L. Leibel et, al, Diabetes, 64 (7): 2299-2309, 2015).

At present, although many pharmaceutical companies and research institutes are developing multispecific drugs based on natural incretin sequences, there is still a lack of drugs with excellent clinical effects. Therefore, there is a need for further research and development in this aspect in the field.

SUMMARY

The present disclosure provides an incretin analogue and a preparation method therefor and a use thereof.

In a first aspect of the present disclosure, provided is an incretin analogue, which includes a glucagon-like polypeptide and a long-chain fatty acid linked to the glucagon-like polypeptide; the amino acid sequence of the glucagon-like polypeptide is shown in Formula (I): YSEGTFTSDX$_{10}$ SKYLDSQAAQDFVQWLLAGGPSSGAPPPS (I) (SEQ ID NO: 2);

X$_{10}$ of the amino acid sequence of SEQ ID NO: 2 is Lysine, the C-terminus of the amino acid sequence of SEQ ID NO: 2 is hydroxy or amino group.

In a preferred embodiment, the long-chain fatty acid is a fatty acid containing 14 to 20 carbons, preferably a fatty acid containing 16 to 18 carbons; more preferably, the long-chain fatty acid is a linear saturated monocarboxylic acid; more preferably, the long-chain fatty acid is palmitic acid.

In another preferred embodiment, the long-chain fatty acid is linked to a Lysine of the glucagon-like polypeptide; preferably, the long-chain fatty acid is linked to the amino acid at X$_{10}$; preferably, the linking is conjugation.

In a preferred embodiment, the glucagon-like polypeptide is linked to the long-chain fatty acid via a linker; preferably, the linker is capable of reacting with the Lysine, and is capable of reacting with active groups of the long-chain fatty acid.

In a preferred embodiment, the linker includes at least 1 (e.g, 1 to 6) unit of -gamma-glutamyl-(-gamma-Glu-).

In a preferred embodiment, the structure of the incretin analogue is shown in Formula (II):

(SEQ ID NO: 6)

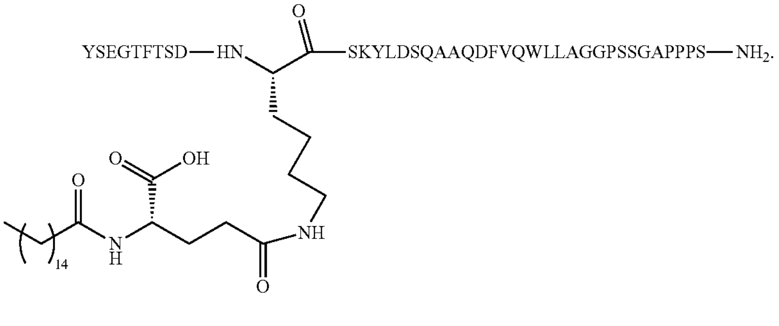

In another aspect of the present disclosure, provided is a use of the incretin analogue in the preparation of a composition, and the composition is used for:

activating human glucagon-like peptide-1 receptors (GLP-1Rs), glucose-dependent insulinotropic polypeptide receptors (GIPRs) and/or glucagon receptors (GCGRs);

preventing, alleviating or treating metabolic diseases; or reducing food intake, reducing fat, reducing body weight or lowering blood glucose.

In a preferred embodiment, the reducing food intake, reducing fat, reducing body weight or lowering blood glucose may be for non-therapeutic purposes.

In a preferred embodiment, the metabolic diseases include: hyperglycemia-associated metabolic diseases or hyperlipemia-associated metabolic diseases.

In another preferred embodiment, the hyperglycemia-associated metabolic diseases include: diabetes or diabetes-associated metabolic syndromes; preferably, the diabetes-associated metabolic syndromes include insulin resistance, glucose intolerance.

In another preferred embodiment, the hyperlipemia-associated metabolic diseases include: obesity, hyperlipemia, fatty liver, hypertriglyceridemia, hypercholesteremia, low HDL cholesterol, high LDL cholesterol; preferably, the fatty liver includes nonalcoholic fatty liver disease (NAFLD), more preferably includes nonalcoholic steatohepatitis (NASH).

In another aspect of the present disclosure, provided is a composition, which includes the above incretin analogue, and a carrier; the carrier is a pharmaceutically, foodologically or nutraceutically acceptable carrier.

In a preferred embodiment, the incretin analogue is in an effective amount.

In another preferred embodiment, the composition includes, but not limited to: a pharmaceutical composition, a food composition or a nutraceutical composition, etc.

In another aspect of the present disclosure, provided is a glucagon-like polypeptide used for preparing the incretin analogue whose amino acid sequence is shown in Formula (I):

(I) (SEQ ID NO: 2)
$YSEGTFTSDX_{10}SKYLDSQAAQDFVQWLLAGGPSSGAPPPS$;

$X_{10}$ of the amino acid sequence of SEQ ID NO: 2 is Lysine (K), the C-terminus of the amino acid sequence of SEQ ID NO: 2 is hydroxy or amino group.

In another aspect of the present disclosure, provided are polynucleotides encoding the glucagon-like polypeptide, expression vectors containing the polynucleotide and/or recombinant cells containing the polynucleotide.

In another aspect of the present disclosure, provided is a preparation method for the incretin analogue, including: conjugating the glucagon-like polypeptide to a long-chain fatty acid.

In another aspect of the present disclosure, provided is a method for non-therapeutically reducing food intake, reducing fat, reducing body weight or lowering blood glucose, which includes giving subjects in need of reducing food intake, reducing fat, reducing body weight or lowering blood glucose the incretin analogue, or the composition.

In another aspect of the present disclosure, provided is a pillbox, including: the incretin analogue; or including: the composition.

Other aspects of the present disclosure will be apparent to persons skilled in the art from the disclosure herein.

DETAILED DESCRIPTION OF THE PREFERRED EMBODIMENTS

Figure 1:
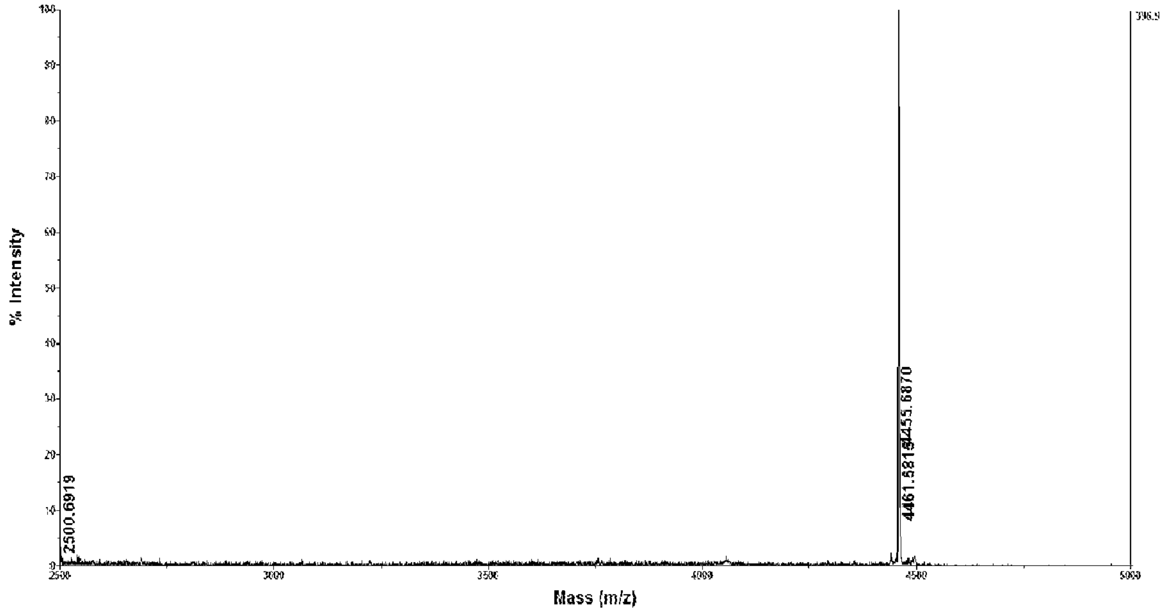
FIG. 1 shows the mass spectrometry results of an incretin analogue P3YELAN.

In view of some deficiencies in the incretin drugs in the prior art, the inventors, on the basis of in-depth research, provide an incretin analog with GLP-1R/GIPR/GCGR agonist activity, which is a triple agonist with significant effects in terms of lowering blood glucose, reducing fat and reducing weight. The present disclosure also provides a preparation method therefor and a use thereof.

Incretin analogue and preparation thereof.

The present disclosure provides an incretin analogue, which includes a glucagon-like polypeptide and a long-chain fatty acid linked to the glucagon-like polypeptide.

The sequence of the glucagon-like polypeptide for constructing the incretin analogue is (SEQ ID NO: 2): YSEGT $FTSDX_{10}SKYLD$ SQAAQ DFVQW LLAGG PSSGA PPPS (I)

where $X_{10}$=K, the C-terminus is OH or $NH_2$.

The glucagon-like polypeptide in the present disclosure may be a recombinant polypeptide, a synthetic polypeptide. The glucagon-like polypeptide may be a chemically-synthesized product, or be produced from prokaryotic or eukaryotic hosts (e.g., bacteria, yeasts, higher plants, insects and mammalian cells) by use of a recombinant technology.

The present disclosure also includes fragments, derivatives and analogues of the glucagon-like polypeptide as shown in SEQ ID NO: 2. As used herein, the terms "fragments", "derivatives" and "analogues" refer to polypeptides that maintain substantially the same biological function or activity of the glucagon-like polypeptide. The polypeptide fragments, derivatives or analogues may be (i) polypeptides with one or more (e.g, 1-5, 1-3 or 1-2) conservative or non-conservative amino acid residues (preferably, conservative amino acid residues) being substituted, while such substituted amino acid residues may or may not be encoded by genetic code, or (ii) polypeptides with substituted groups at one or more (e.g, 1-5, 1-3 or 1-2) amino acid residues, or (iii) polypeptides formed by fusing an additional amino acid sequence into the polypeptide sequence (e.g, a leader sequence or a secretory sequence or a sequence used to purify the polypeptides or a proprotein sequence, or a fusion protein). According to the definitions herein, such fragments, derivatives and analogues are well known to those skilled in the art.

In the present disclosure, also included are polypeptides having amino acid sequence identity of 75% or above (preferably, at least 80%, 85%, 90%, 95%) with the glucagon-like polypeptide as shown in SEQ ID NO: 2, and having the functions of the glucagon-like polypeptide as shown in SEQ ID NO: 2.

In the present disclosure, also included are modified polypeptides formed by modifying one or several amino acids with purposes of increasing the stability, half-life and efficacy of the polypeptide (generally without changing the primary structure), including: chemically derivatized forms, such as acetylation or carboxylation, of polypeptides in vivo or in vitro. Modification also includes glycosylation. Modified forms also include sequences including phosphorylated amino acid residues (e.g, phosphotyrosine, phosphoserine, phosphothreonine). Also involving are polypeptides which have been modified so as to improve the hydrolysis resistance or optimize the solubility.

The present disclosure also provides polynucleotide sequences encoding the glucagon-like polypeptide of the present disclosure or the conservative variant polypeptides thereof. The polynucleotides of the present disclosure can be in a form of DNA or RNA. DNA can be a coding chain or a non-coding chain. That is, "polynucleotides encoding the polypeptides" may be polynucleotides encoding this polypeptide, also may be polynucleotides including additional coding and/or non-coding sequences.

The present disclosure also relates to an expression vector including the polynucleotide of the present disclosure, and a host cell genetically produced from the expression vector or the coding sequence of the glucagon-like polypeptide, as well as a method for producing the polypeptide by a recombinant technology.

The present disclosure also provides a use of the glucagon-like polypeptide in preparing the incretin analogue of the present disclosure.

The long-chain fatty acid for constructing the incretin analogue is a fatty acid containing 14 to 20 carbons, preferably a fatty acid containing 16 to 18 carbons. In the present disclosure, also included esters, ethers or derivatives of the long-chain fatty acid, and also included are salts of the long-chain fatty acid (e.g., sodium salts). In a preferable implementation of the present disclosure, the long-chain fatty acid is a linear saturated monocarboxylic acid.

As a preferable implementation of the present disclosure, the linking is chemical conjugation. In order to achieve the purpose of chemical conjugation, lysine (K) or cysteine (C) was introduced compared to the original sequence of the polypeptide, and the fatty acid was conjugated to lysine (K) or cysteine (C).

The activity of the glucagon-like polypeptide conjugated to long-chain fatty acid is obviously improved and the half-life of the drug in vivo is significantly prolonged. Preferably, tyrosine (Y) at position 10 is mutated to lysine (K) (in Formula I; $X_{10}$=K), so that the fatty acid chain can be conjugated to the polypeptide fragments of the incretin analogue through lysine (K).

In preferable embodiments of the present disclosure, in the incretin analogue as provided in the present disclosure, the fatty acid chain is palmitic acid (C16), a linear monocarboxylic acid with chemical structural formula as shown below:

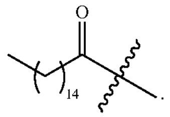

In the incretin analogue as provided in the present disclosure, a linker can be further provided between the glucagon-like polypeptide fragment and the long-acting carrier. The linker may generally have reaction with the lysine residue K and/or the cysteine residue C on the glucagon-like polypeptide fragment, and with active groups on the long-acting carrier (for example, the linker may include carboxyl, maleimide and other active groups) respectively, so that two terminals of the linker are respectively cross-linked to the long-acting carrier and the polypeptide fragment of the incretin analogue for conjugation process for example, the type of cross-linking can be various types of condensation.

The linker may be various kinds of linker in the field suitable for linking the polypeptide fragment of the incretin analogue to the long-acting carrier. In some specific examples of the present disclosure, the linker can be -γGlu- (-gamma-glutamyl- or -γE) with chemical structural formula as shown below:

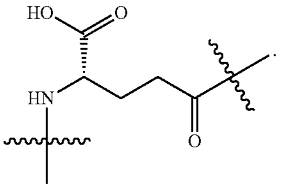

-γGlu-

As described above, the C-terminal amino acid of the incretin analogue as provided in the present disclosure may be modified, for example, amidated. The amidation generally refers to transforming the C-terminal-COOH group into a $—CONH_2$ group, for example, in Formula (I): the C-terminus is $NH_2$.

In some specific examples of the present disclosure, the specific sequence of the incretin analogue is shown in SEQ ID NO: 6 in Table 1. In Table 1, the sequence alignment of the polypeptide fragment with Glucagon (SEQ ID NO: 1, simply referred as GCG), GLP-1 (SEQ ID NO: 3) and GIP (SEQ ID NO: 4) is also presented.

TABLE 1

| SEQ ID NO: | Name of poly-peptide | Sequence (or modified sequence) |
|---|---|---|
| 1 | Glucagon | HSQGT FTSDY SKYLD SRRAQ DFVQW LMNT (SEQ ID NO: 1) |
| 3 | GLP-1 | HAEGT FTSDV SSYLE GQAAK EFIAW LVKGRG (SEQ ID NO: 3) |
| 4 | GIP | YAEGTFISDYSIAMDKIHQQDFVNWLLAQKGKKNDWK HNITQ (SEQ ID NO: 4) |
| 5 | YELAN | YSEGT FTSDY SKYLD SQAAQ DFVQW LLAGG PSSGA PPPS-OH (SEQ ID NO: 5) |
| 6 | P3YELAN | YSEGT FTSD$X_{10}$ SKYLD SQAAQ DFVQW LLAGG PSSGA PPPS-$NH_2$; (SEQ ID NO: 6) $X_{10}$ = K (palmitoyl-γE) |
| 7 | P5YELAN | YSEGT FTSD$X_{10}$ SKYLD SQAAQ DFVQW LLAGG PSSGA PPPS-$NH_2$ (SEQ ID NO: 7); $X_{10}$ = K (((octadecanedioic acid monoacyl)-γE)-2xOEG) |
| 8 | P9YELAN | YSEGT FTSD$X_{10}$ SKYLD SQAAQ DFVQW LLAGG PSSGA PPPS-$NH_2$ (SEQ ID NO: 8); $X_{10}$ = K (((eicosandioic acid monoacyl)-γE)-2xOEG) |

In Table 1, -γE- is -gamma-Glu (-gamma-glutamyl-), "γE-C16" means that palmitoyl is conjugated onto epsilon-nitrogen of lysine through a -gamma-glutamyl-linker. "2×OEG" means that two -OEG-(−2-(2-(2-aminoethoxy) ethoxy)acetyl-) are linked.

The present disclosure also provides a preparation method of the incretin analogue, which includes linking the glucagon-like polypeptide with a long-chain fatty acid.

The preparation method may include: preparing the incretin analogue by a chemical synthesis method. The preparation method may also include: culturing suitable host cells under suitable conditions to express the polypeptide fragments of the incretin analogue, separating and purifying to obtain the polypeptide fragments of the incretin analogue, then chemically crosslinking the long-acting carrier to the polypeptide fragments of the incretin analogue. The incretin analogue of the present disclosure can be prepared by a standard peptide synthesis method, for example, by standard solid phase or liquid phase methods, stepwise or by fragment assembly, and separating and purifying the resulting polypeptide fragments of the incretin analogue as well as the incretin analogue products, or by any combination of recombinant and synthesis methods.

Use of the Incretin Analogue

The present disclosure also provides uses of the incretin analogue in the preparation of drugs of GLP-1R/GIPR/GCGR multiple agonist for treating metabolic diseases. The metabolic diseases specifically can be selected from diabetes, obesity, dyslipidemia, nonalcoholic fatty liver disease (NAFLD)/nonalcoholic steatohepatitis (NASH), other metabolic syndromes associated with diabetes, including high triglycerides, low HDL cholesterol and high LDL cholesterol, insulin resistance, obesity or glucose intolerance, etc. The present disclosure also provides a method for treating diseases, including administering to an individual the incretin analogue as provided in the first aspect of the present disclosure. In random blood glucose assay tests, the effects of lowering blood glucose and reducing weight in diabetes model mice who have been administered with the incretin analogue of the present disclosure are obviously superior to those in the samples of control group.

In addition to being used in the prevention, alleviation or treatment of diseases, the incretin analogue of the present disclosure can also be used in some non-therapeutic aspects. It can be seen from partial results of examples according to the present disclosure that, the incretin analogue is capable of reducing food intake, reducing fat, reducing body weight or lowering blood glucose very significantly. Therefore, the incretin analogue of the present disclosure can also be applied in subjects who do not yet have disease characteristics, but have a need for food intake control, fat reduction, and weight loss.

Although in the prior art, molecules with multiple agonist activities have been researched and developed in the field, it is actually very difficult to obtain an ideal drug of this type. The first issue is safety, especially the issue of immunogenicity. Blood glucose-lowering and weight-loss drugs require long-term use, so they have extremely high requirements for safety. In order to design and obtain a polypeptide with high multiple agonist activities and in vivo stability, many mutation sites, nonnatural amino acids and other modifications are often introduced in prior art solutions. The introduction of these mutations and nonnatural amino acids all increase the risk of potential immunogenicity. With regard to drugs for treating such diseases as diabetes and obesity, safety is extremely important. Moreover, for small peptides of about 30 amino acids in length such as GLP-1 and Glucagon, changes in sequence can easily affect their activities; while for multi-active polypeptides, the changes are more complicated due to the agonism of multiple different receptors, so it is impossible to predict the consequences of their agonist activities on the receptors after the changes of any one amino acid. For example, Joseph Chabenne et, al. reported that (Joseph Chabenne et, al., Molecular Metabolism, 3:293-300, 2014) in the alanine scan (Ala scan) of GCG, after each site of GCG is independently substituted with alanine, the relative residual activity retention spans from 0.2% to 100%; and indicated that mutations at positions 1, 2, 3, 4, 6-12, 14, 15, 22, 23, 25-27, 29 of GCG could substantially reduce the GCGR agonist activity (Table 4 in the article). However, it can be seen from other reports that when single or several of the above sites are mutated simultaneously and substituted with other amino acids, the changes in activity are not always consistent with the results of the Ala scan. As reported by Jonathan W Day et, al. (Jonathan W Day et, al., Nature Chemical Biology, 5:749-757, 2009), when different mutations such as 16S→G, 16S→T, 16S→H, 16S→E are carried out on the position 16 of GCG, the GCGR agonist activity is improved instead, which completely contradicts the alanine scan results of Joseph Chabenne. Secondly, Joseph Chabenne believed through research that, substitution with alanine at position 23 will result in an almost complete loss of GCGR agonist activity (only retaining 1.1%); while Jonathan W Day mutated position 23 into Ile, and its GCG activity does not decrease. Further for example, the Ala scan results suggested that the S at position 2 was very important for retaining the GCG activity (only ⅓ of the activity was retained when it was mutated to Ala), but Brian Finan et, al. reported that (Finan B et, al., Nat Med. 2015; 21:27-36), when 2S→Aib, 2S→Ser, 2S→G, 2S→dAla substitution mutations were performed on the amino acid at position 2 of GCG, in combination with the mutations at other sites, the relative agonist activity of GCGR was instead improved to 200% to 640%. It was also found in the research of the present inventors that, when some mutations which are beneficial to improve the activity of GLP-1, GCG or GIP were introduced in combinations, the effects were often completely inconsistent with those of a single site mutation. In addition, the biological activity of GLP-1, Exendin-4, GCG or GIP and such polypeptides would be affected when there was an increase or decrease of amino acids at the N and/or C-terminal. If one or two amino acids were removed from the N-terminal, the agonist activity of GLP-1, GCG, and the like will be completely lost. For example, Oxyntomodulin only has 8 amino acids of KRNRNNIA more than Glucagon at the C-terminal, its GCGR agonist activity is lost by about 90% (Alessandro Pocai et, al., Diabetes; 58 (10): 2258-2266, 2009; Henderson S J et, al., Diabetes Obes Metab, 2016).

The incretin analogue of the present disclosure has very high GLP-1R and GIPR agonist activity and weaker GCGR agonist activity. Surprisingly, the in vitro activity of the incretin analogue polypeptides changes significantly before and after crosslinking with a fatty acid.

The embodiments of the present disclosure will be illustrated through specific examples below. Other advantages and effects of the present disclosure can be easily understood by persons skilled in the art from the contents disclosed in this specification. The present disclosure can also be implemented or applied through other different specific embodiments. Various details in the specification can also be modified or changed based on different viewpoints and applications without departing from the spirit of the present disclosure.

Composition

The present disclosure also provides a composition, which contains an effective amount of the incretin analogue of the present disclosure and a carrier. The carrier is a pharmaceutically, foodologically or nutraceutically acceptable carrier. The composition includes, but not limited to: a pharmaceutical composition, a food composition or a nutraceutical composition, or the like.

In the present disclosure, the pharmaceutical composition may contain 0.01-95% (e.g., 0.1%, 1%, 5%, 10%, 20%, 30%, 50%, 80%, etc.) by weight of the incretin analogue.

As used herein, "pharmaceutically, foodologically or nutraceutically acceptable" ingredients are substances which are suitable for human and/or animals without undue adverse side effects (such as toxicity, irritation and allergic reaction), that is, with reasonable benefit/risk ratio; for example, pharmaceutical carriers or excipients commonly used in the field.

As used herein, "effective amount" or "effective dose" refers to an amount as used herein that can produce functions or activities on human and/or animals and can be accepted by human and/or animals.

The pharmaceutical composition of the present disclosure may be in various dosage forms, as long as being capable of enabling the active ingredients to effectively reach mammalian organism. For example, the dosage forms may be selected from: gels, aerosols, tablets, capsules, powder, granules, syrup, solution, or suspension. According to the types of diseases treated by the compound of the present disclosure, the skilled in the art can choose a dosage form that is convenient for application.

Suitable pharmaceutically acceptable carriers are well known to those with ordinary skills in the art. A full description of pharmaceutically acceptable carriers can be found in Remington's Pharmaceutical Sciences (Mack Pub. Co., N.J. 1991). The pharmaceutically acceptable carrier in the composition may include liquid, such as water, phosphate buffer, ringer solution, normal saline, balanced salt solution, glycerin or sorbitol, etc. In addition, these carriers may also contain auxiliary substances, such as lubricants, glidants, wetting agents or emulsifiers, pH buffer substances and stabilizers, e.g., albumin, etc.

For ease of preparation and administration, preferable pharmaceutical compositions are solid compositions, especially tablets and solid-filled or liquid-filled capsules. The compound or pharmaceutical composition of the present disclosure may also be stored in sterilized instruments suitable for injection or instillation.

The effective administration dose of the incretin analogue of the present disclosure as the active ingredients may change with the administration mode and the severity of the diseases to be treated, for example, it may be given at a dosage of about 0.00001-10 mg/kg body weight per day. The dosing frequency can also be adjusted, for example, with regard to administration in sustained-release form, the drugs may be administered every other day or at intervals of several days. The dosing scheme can be adjusted so as to provide optimal therapeutic responses.

When applied to large animals and patients, the effective dosage of the composition for large animals and humans can be converted from the dosage used in small animals through corresponding professional conversion formulas (including the dosage conversion of solid or solution forms). In specific examples of the present disclosure, some dosing schemes with regard to animals such as mice are given. It is easy for those skilled in the art to convert the dosage for animals such as mice to the dosage suitable for using in humans, for example, the calculation may be based on Meeh-Rubner formula: Meeh-Rubner formula: $A=k\times(W2/3)/10,000$. Where, A is body surface area, in $m^2$; W is body weight, in g; K is a constant, varying with the species of animals, generally 9.1 for mice and rats, 9.8 for guinea pigs, 10.1 for rabbits, 9.9 for cats, 11.2 for dogs, 11.8 for monkeys, and 10.6 for humans. It should be understood that, the conversion of dosages can be varied according to different drugs and clinical insituations as well as the evaluation of experienced pharmacists.

The present disclosure also provides a pillbox or kit, which includes: the incretin analogue; or the pharmaceutical composition. For ease of clinical application, the pillbox or kit of the present disclosure can also contain other auxiliary accessories, e.g., injectors, etc. Instructions for use may also be included in the pillbox or kit, so that persons skilled in the art can use it in a correct manner.

Before further describing the implementation of the present disclosure, it should be understood that, the protection scope of the present disclosure is not restricted to the following specific embodiments; it should also be understood that, the terms used in the examples of the present disclosure are for describing specific embodiments, rather than for restricting the protection scope of the present disclosure.

When numerical ranges are given in the examples, it should be understood that, unless otherwise indicated in the present disclosure, both endpoints of each numerical range and any value between the two endpoints can be selected. Unless otherwise defined, all technical and scientific terms used herein have the same meanings as commonly understood by those skilled in the art. In addition to the specific methods, equipment and materials used in the embodiments, according to the mastery of the prior art by those skilled in the art and as documented in the present disclosure, any methods, equipment and materials of the prior art similar or equivalent to the methods, equipment and materials described in embodiments of the present disclosure can be used to implement the present disclosure.

Unless otherwise indicated, the experimental methods, detection methods, and preparation methods disclosed in the present disclosure all employ conventional techniques of molecular biology, biochemistry, chromatin structure and analysis, analytical chemistry, cell culture, recombinant DNA technology as well as conventional techniques in related fields. These techniques have been fully illustrated in existing documents, specifically see Sambrook et, al., MOLECULAR CLONING: A LABORATORY MANUAL, Second edition, Cold Spring Harbor Laboratory Press, 1989 and Third edition, 2001; Ausubel et, al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECULAR BIOLOGY, Vol. 119, Chromatin Protocols (PBBecker, ed.) Humana Press, Totowa, 1999, and the like. The meanings of the abbreviations involved in the examples are as follows:

RT: room temperature;
DMF: N,N-dimethylformamide;
Fmoc: 9H-fluoren-9-ylmethoxycarbonyl;
Trt: trityl;
Boc: tert-butoxycarbonyl;
HOBt: 1-hydroxybenzotriazole;
tBu: tert-butyl;
DCM: dichloromethane;
DBLK: 20% N,N-dimethylformamide piperidine;
DIC: N,N'-diisopropylcarbodiimide;
MeOH: methanol;
TFA: trifluoroacetic acid;
Fmoc-Lys (Pal-Glu-OtBu)-OH: $N^{\alpha}$-fluorenemethoxycarbonyl-($N^{\epsilon}$-(gamma-glutamyl ($N^{\alpha}$-hexadecyl, α-tert-butyl ester))) lysine;
-γE-: -γ-glutamyl-;
-OEG-: -2-(2-(2-aminoethoxy)ethoxy)acetyl-
DIEA: N,N-diisopropylethylamine;
MTBE: methyl tert-butyl ether;
TFEA: 2,2,2-trifluoroethanol;
$Pd(PPh_3)_4$: tetrakis(triphenylphosphine) palladium;
Alloc: allyloxycarbonyl.

For various commercially available amino acids and amino acid fragments, as well as various commercially available resins involved in the examples, their manufacturers and product models are as follows:

Fmoc-protected amino acid raw materials, 2-CTC resin and Rink amide MBHA resin are all conventional commercial reagents (Manufacturer of protected amino acids: Chengdu zyiochemical Technology Co., Ltd.; Manufacturer of resins: Tianjin Nankai HECHENG S&T Co., Ltd.);

Organic solvents and other sources of raw materials are all commercially available (Manufacturer: Sinopharm Chemical Reagent limited corporation; chemically pure).

Additionally, conditions for HPLC and mass spectrometry as well as models and manufacturers of equipment used are illustrated as follows:

Instrument: HPLC UltiMate 3000; the detection conditions are shown in Table 2 below.

TABLE 2

| | | | | | | | |
|---|---|---|---|---|---|---|---|
| Chromatographic column | JUPITER ® 4 um Proteo 90 Å 4.6*250 mm . . . | | | | | | |
| Mobile phase | A: TFA:purified water = 1:1000<br>B: TFA:acetonitrile = 1:1000 | | | | | | |
| Detection parameters | Flow rate: 1.0 ml/min, Wavelength: 220 nm, Column temperature: 45° C. | | | | | | |
| | Elution gradient | | | | | | |
| | T (min) | 0 | 40 | 41 | 46 | 47 | 55 |
| | A (%) | 75 | 35 | 10 | 10 | 75 | 75 |
| | B (%) | 25 | 65 | 90 | 90 | 25 | 25 |

Preparative liquid phase: Beijing Tong Heng Innovation Technology Co., Ltd., LC3000.

Mass spectrometry: Instrument model is 5800 MALDI-TOF-TOF (AB SCIEX), the analysis software is TOF/TOF Explorer, Data Explorer, MS employs Reflector Positive parameters: CID (OFF), mass rang (700-6500 Da) Focus Mass (1200 Da) Fixed laser intensity (5600) Digitizer: Bin Size (0.5 ns).

Example 1. Preparation of Incretin Analogues

1. Preparation of an Incretin Analogue P3YELAN

The structure of the incretin analogue P3YELAN is as below:

(SEQ ID NO: 6)

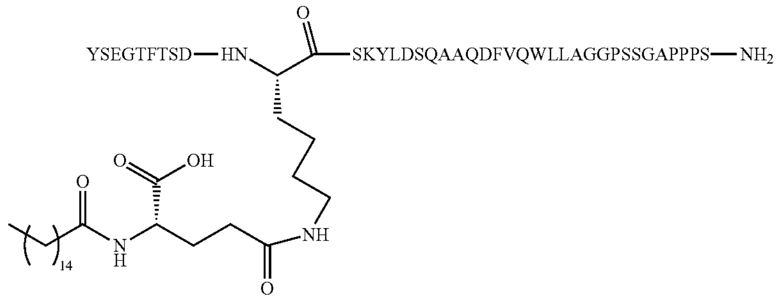

that is: YSEGT FTSD$X_{10}$ SKYLD SQAAQ DFVQW LLAGG PSSGA PPPS-$NH_2$ (SEQ ID NO: 6)

$X_{10}$=K (palmitoyl-γE).

Synthesis of Fmoc-Ser (tBu)-Rink Amide MBHA Resin:

2.65 g of Rink amide MBHA resin (Tianjin Nankai HECHENG S&T Co., Ltd.) with a degree of substitution of 0.38 mmol/g was weighed, added into a solid-phase reaction column, swelled with 10 mL DCM for 30 minutes, and then washed with 10 mL DMF for 3 times. Into the reaction column was added 15 mL DBLK solution to react for 5 minutes. Then the resin was filtrated, and washed once with 20 mL DMF. 15 mL DBLK solution was additionally added to react for 10 minutes, and detected by Kaiser as positive. The reaction solution was filtrated, and washed 3 times with 20 mL DMF per time.

1.91 g Fmoc-Ser (tBu)-OH and 0.81 g HOBt were dissolved with 10 mL DMF, and activated with 0.69 g DIC for 5 min at 5 to 8° C. They were then added into the above reaction column filled with resin to react for 2 hours. After being detected by Kaiser as negative, the obtained resin was directly used in the next step of synthesizing peptide resins.

Synthesis of Peptide Resins:

The above resin Fmoc-Ser (tBu)-Rink amide MBHA resin (1.0 mmol) was weighed, added into a reaction column and swelled with 20 mL DCM for 30 minutes, then washed 3 times with 20 mL DMF per time. After washing, into the reaction column was added 10 mL DBLK solution (20% piperidine/DMF (V/V)) to react for 5 minutes, then filtrated, and washed once with 20 mL DMF. 10 mL DBLK solution (20% piperidine/DMF (V/V)) was additionally added to react for 10 minutes, and detected by Kaiser as positive. The reaction solution was filtrated, and washed 3 times with 20 mL DMF per time. Fmoc-Pro-OH (1.69 g, 5.0 eq) and HOBt (0.81 g, 6.0 eq) were dissolved with 10 mL DMF, and activated by DIC (0.69 g, 5.5 eq) for 5 min at 5 to 8° C., then added into the reaction column to react for 1 hour, and detected by Kaiser as negative. Upon completion, the reaction was washed 3 times with 20 mL DMF per time. By repeating the above deprotection and coupling operations, other amino acids were coupled in turns according to the sequence of the peptide, where $X_{10}$ was coupled with Fmoc-Lys (Pal-Glu-OtBu)-OH (Chengdu zyiochemical Technology Co., Ltd.). After the completion of the coupling of the last amino acid, deprotection was conducted following the above deprotection method. After the completion of deprotection, it was successively washed with DMF twice, washed with MeOH twice, washed with DCM twice and washed with MeOH twice, by 20 mL for each washing solvent. The materials were collected, dried at normal temperature and at reduced pressure to get the target peptide resin.

Cleavage of Crude Peptides:

5.02 g of the above peptide resin was weighed, slowly added into 60 mL lysis solution (trifluoroacetic acid: thioanisole: anisole: ethanedithiol=90:5:3:2) at 20-30° C., and reacted for 2 hours after the completion of addition. Upon the completion of reaction, resin was removed by filtration. The filtrate was poured into pre-cooled methyl tert-butyl ether (600 mL) under vigorous stirring. The resulting mixed solution was placed in a refrigerator to settle for 2 hours. After removing the supernatant, the solution was washed 5 times with 400 mL pre-cooled methyl tert-butyl ether per time by centrifugation. After completion, the materials were collected, dried in vacuo at normal temperature to get 2.23 g crude peptides.

Purification of Crude Peptides:

The crude peptides were refined by multi-step purification using preparative liquid phase (Beijing Tong Heng Innovation Technology Co., Ltd., LC3000): Step 1: stationary phase: C18 (Daisogel: sp-120-40/60-C18-RPS), mobile phase: 0.1% TFA, acetonitrile; Step 2: stationary phase: C8 (Daisogel: sp-120-10-C8-P), mobile phase: 0.5% phosphoric acid, acetonitrile; Step 3: stationary phase: C8 (Daisogel: sp-120-10-C8-P), mobile phase: 50 mM ammonium acetate, 0.3% acetic acid, acetonitrile, and finally lyophilized (using a lyophilizer commercially available from Beijing boyikang Lab Instrument Co., Ltd., FD-2A) to get fine peptide (98.0%). MS was finally employed to determine the exact molecular weight of the fine peptide: m/z 4455.69 $(M+H)^+$. MS was shown in FIG. 1.

2. Preparation of a Glucagon Derivative P5YELAN

The structural formula of the glucagon derivative P5YELAN is as below:

(SEQ ID NO: 7)

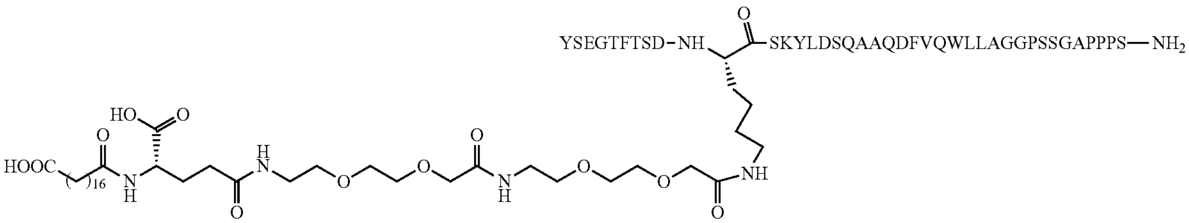

that is: YSEGT FTSD$X_{10}$ SKYLD SQAAQ DFVQW LLAGG PSSGA PPPS-NH2 (SEQ ID NO: 7)

$X_{10}$=K (((octadecanedioic acid monoacyl)-γE)-2×OEG)

Synthesis of branched-chain-protected amino acid W1 by a solid phase method: Alloc-Lys ((Octadecanedioic Acid mono-tert-butyl ester)-γGlu-OtBu)-OEG-OEG)-OH, of which the structure is as below:

W1

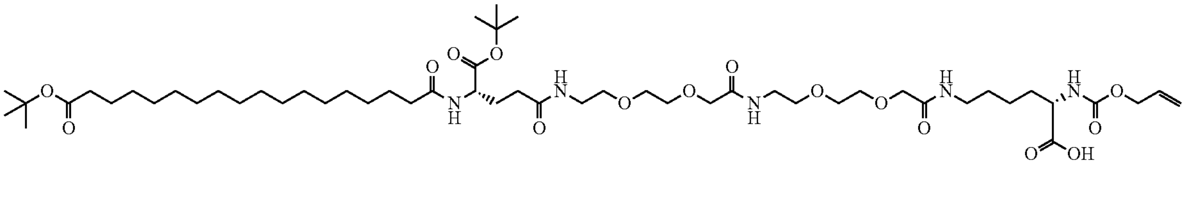

Synthesis of W1:

20 g of 2-CTC resin with a degree of substitution of 1.0 mmol/g was added into a solid-phase reaction column, and washed once with DMF. After swelling the resin with DMF for 30 minutes, 8.53 g Alloc-Lys (Fmoc)-OH (20 mmol) was dissolved in DMF, activated by adding 7.5 ml DIEA (45 mmol) under an ice-water bath, and then added into the above reaction column filled with resin. After reaction for 2 hours, 30 ml absolute methanol was added to block for 1 hour, and then Fmoc-protected resin was washed 3 times with DMF and deprotected with a mixed solution of DMF: pyridine at a volume ratio of 4:1. The deprotected resin was washed 6 times with DMF. 15.42 g [2-[2-(Fmoc-amino) ethoxy]ethoxy]acetic acid and 5.41 g HOBt were dissolved with DMF, activated by subsequent addition of 6.2 ml DIC under an ice-water bath, and then transferred to the above reaction column filled with resin and reacted at room temperature for 2 hours. By repeating the above steps of removing Fmoc protection and adding corresponding materials for coupling, [2-[2-(Fmoc-amino) ethoxy]ethoxy]acetic acid, Fmoc-Glu-OtBu, and octadecanedioic acid mono-tert-butyl ester were coupled in turns according to the order of branched-chain fragments. After the completion of coupling, the resin was washed 3 times with DMF, washed 5 times with MeOH, and drained. The resin was added into 400 ml of TFEA/DCM=1:4 to react at room temperature for 4 h. After the resin was filtered, the filtrate was spun to remove DCM, then added into 500 ml MTBE for settlement, and centrifugally dried to give 19.43 g of a target compound with m/Z 1242.51 (M+H)+.

The synthesis of polypeptides was the same as that of P3YELAN, where $X_{10}$ was coupled with W1, and the Alloc group was removed with $Pd(PPh_3)_4$. The resulting crude peptide was purified by RP-HPLC and finally lyophilized to get the fine peptide (96.5%). MS was used to determine the exact molecular weight of the fine peptide: m/z 4804.13 (M+H)+.

3. Preparation of a Glucagon Derivative P9YELAN:

The structural formula of the glucagon derivative P9YELAN is as below:

(SEQ ID NO: 8)

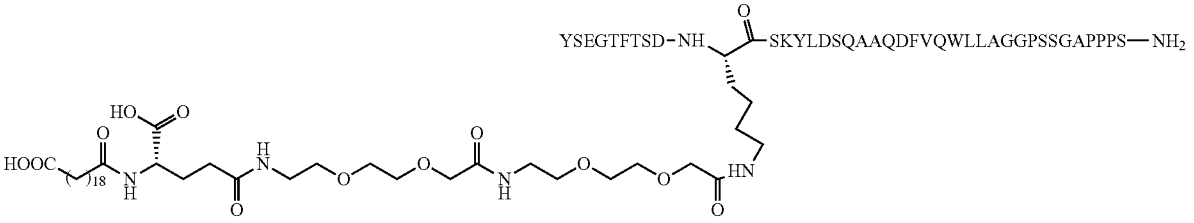

that is: YSEGT FTSDX$_{10}$ SKYLD SQAAQ DFVQW LLAGG PSSGA PPPS-$NH_2$ (SEQ ID NO: 8)

$X_{10}$=K (((eicosandioic acid monoacyl)-γE)-2×OEG)

The synthesis of branched-chain-protected amino acid was the same as that of P5YELAN, in which the branched-chain-protected amino acid W2 namely Alloc-Lys ((Eicosanedioic Acid mono-tert-butyl ester)-γGlu-OtBu)-OEG-OEG)-OH (where eicosandioic acid mono-tert-butyl ester is used for fatty acid coupling) of the structure as below was firstly synthesized by a solid phase method:

W2

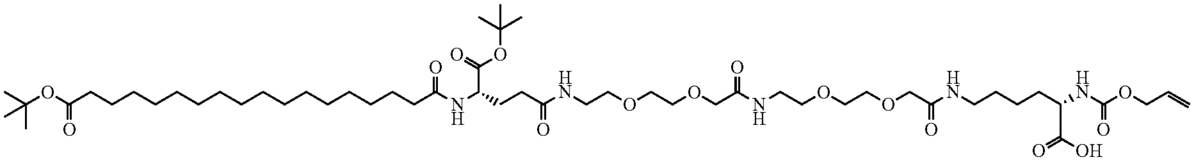

Polypeptides were then synthesized, which was the same as that of P3YELAN, where $X_{10}$ was coupled with W2, and the Alloc group was removed with $Pd(PPh_3)_4$. The resulting crude peptide was purified by RP-HPLC to get the fine peptide (97.1%). MS was used to determine the exact molecular weight of the fine peptide: m/z 4832.50 (M+H)+.

Example 2. In Vitro Cytological Activity Assay

I. GLP-1R Agonist Activity Assay

GLP-1R agonist activity was detected using luciferase reporter gene assay (Jonathan W Day et, al.: Nat Chem Biol. 2009 October; 5 (10): 749-57). Humanized GLP-1R gene was cloned into mammalian cell expression plasmid pCDNA3.1 to construct recombinant expression plasmid pCDNA3.1-GLP-1R, and at the same time, luciferase full-length gene was cloned into pCRE plasmid to get pCRE-Luc recombinant plasmid. The pcDNA3.1-GLP-1R and pCRE-Luc plasmids were transfected into CHO-K1 cells at a molar ratio of 1:10, and the stably transfected cell strains were screened.

Cells were cultured in a 9-cm cell culture dish with DMEM/F12 medium containing 10% FBS and 300 μg/ml G418. When the confluence reached about 90%, the culture supernatant was discarded. The cells were digested in 2 ml trypsin for 3 min and neutralized in 2 ml DMEM/F12 medium containing 10% FBS and 300 μg/ml G418 was added for neutralization, then the mixture was transferred into a 15 ml centrifuge tube. After centrifugation at 1000 rpm for 5 min, the supernatant was discarded. 2 ml DMEM/F12 medium containing 10% FBS and 300 μg/ml G418 was added for resuspension, and the number of cells was counted. Cells were diluted with DMEM/F12 medium containing 10% FBS to $1\times10^5$/ml, and plated in 96-well plates at 100 μl/well, i.e., $1\times10^4$/well. After adherence, the medium was replaced with DMEM/F12 medium containing 0.2% FBS for culture. After discarding the supernatant of the cells in the 96-well plates, the purified glucagon derivatives (the positive control group: Dulaglutide (Trade name: TRULICITY®)) were diluted with DMEM/F12 medium containing 1% BSA to a series of defined concentration, added into cell culture wells at 100 μl/well, and detected after stimulation for 6 h. The samples were detected according to the specification of Lucifersae reporter kit (Ray Biotech, Cat: 68-LuciR-S200). The assay was repeated 3 times for each sample.

II. GIPR Agonist Activity Assay

GIPR agonist activity was also detected using luciferase reporter gene assay. Humanized GIPR gene was cloned into mammalian cell expression plasmid pcDNA3.1 to construct a recombinant expression plasmid pCDNA3.1-GIPR. The transfected CHO-K1 cells and the stably transfected cell strains were constructed as above. The assay steps were the same as above (the positive control group: natural humanized GIP peptides) and the assay was repeated 3 times for each sample.

III. GCGR Agonist Activity Assay

GCGR agonist activity was also detected using luciferase reporter gene assay. Humanized GCGR gene was cloned into mammalian cell expression plasmid pcDNA3.1 to construct a recombinant expression plasmid pCDNA3.1-GCGR. The transfected CHO-K1 cells and the stably transfected cell strains were constructed as above. The assay steps were the same as above (the positive control group: natural humanized GCG peptides) and the assay was repeated 3 times for each sample.

IV. Assay Results

Figure 2:
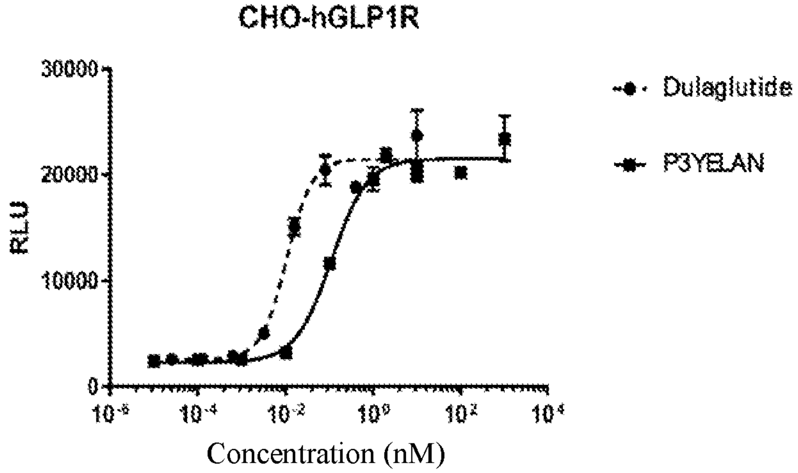
FIG. 2 shows the in vitro GLP-1R agonist activity of the incretin analogue P3YELAN; Dulaglutide was taken as a control.
Figure 3:
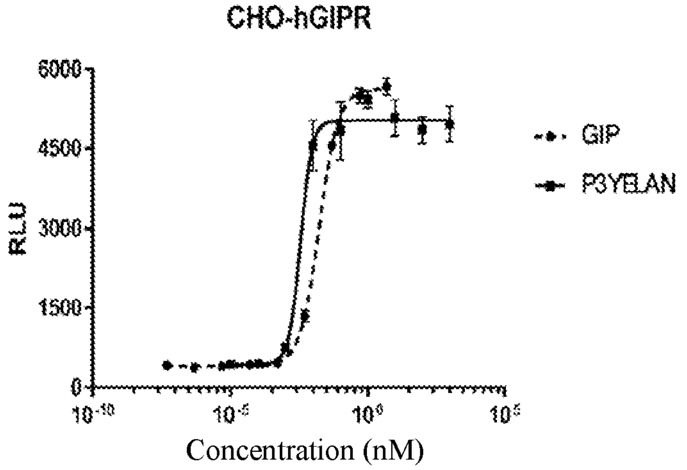
FIG. 3 shows the in vitro GIPR agonist activity of the incretin analogue P3YELAN.
Figure 4:
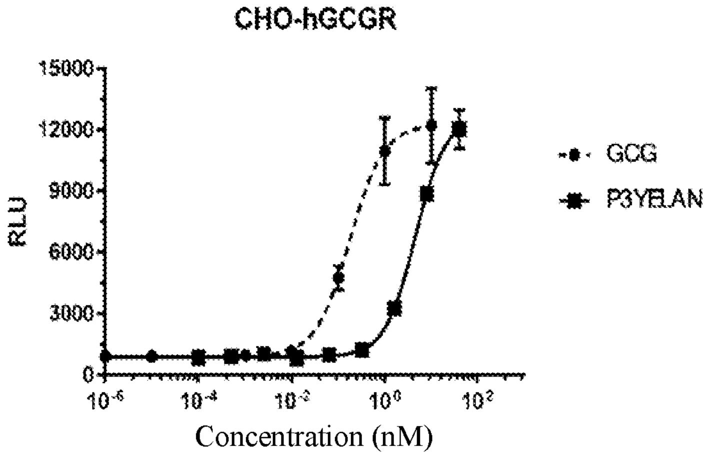
FIG. 4 shows the in vitro GCGR agonist activity of the incretin analogue P3YELAN.

FIGS. 2, 3, 4 show the agonist activity results of GLP-1R, GIPR and GCGR, respectively, and the specific EC50s were shown in Table 3.

TABLE 3

| Code of active protein | GLP-1R agonist activity (EC50, nM) | GIPR agonist activity (EC50, nM) | GCGR agonist activity (EC50, nM) |
|---|---|---|---|
| Dulaglutide | 0.01 | / | / |
| GCG | / | / | 0.17 |
| GIP | / | 0.01 | / |
| P3YELAN | 0.11 | 0.004 | 4.57 |
| P5YELAN | 0.81 | 1.56 | 5.87 |
| P9YELAN | 4.25 | 0.19 | 4.77 |

The above results show that, P3YELAN of the present disclosure has very high GLP-1R and GIPR agonist activities, at the same time it also has significant GCGR agonist activity. However, P5YELAN and P9YELAN with the same peptide sequence have significantly decreased cellular agonist activity due to different conjugated fatty acid chains.

Example 3. Serum Stability

In this example, the serum stability of the incretin analogue P3YELAN was determined by the following steps:

(1) The incretin analogues P3YELAN, YELAN and the control (Dulaglutide) were formulated with 5 mM Tris-HCl, pH 8.5, and 0.02% TWEEN-80 solution into solutions at a concertation of 1.0 mg/ml, which were sterilized and filtered (0.22 μm, Millipore SLGP033RB), then diluted 10-fold with rat serum, mixed evenly and divided into sterile centrifuge tubes;

(2) Three tubes of each of the above samples were cryopreserved at −20° C. as controls, other tubes were placed in a 37° C. incubator, and sampled at 0 hours, 12 hours, 24 hours and 72 hours to detect the activity;

(3) The GLP-1R agonist activity was detected. Relative activity: the activity value at hour 0 is taken as 100%, and the value measured at subsequent time points is obtained by comparing with the activity value at hour 0.

Figure 5:
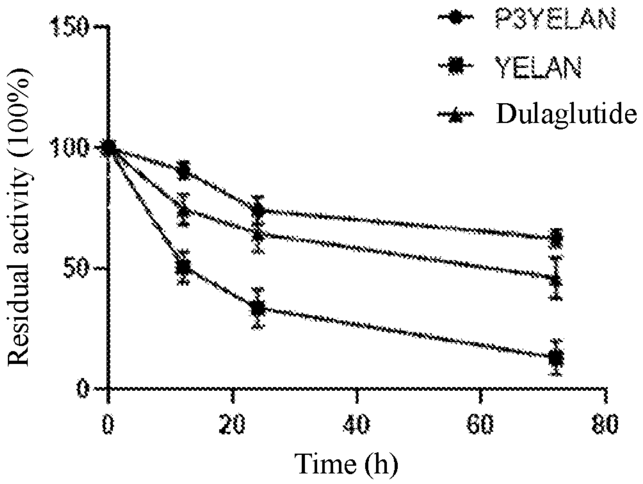
FIG. 5 shows the in vitro serum stability of the incretin analogue P3YELAN; YELAN and Dulaglutide were taken as controls.

FIG. 5 shows the residual activity of the incretin analogue P3YELAN over time. The results show that, compared with YELAN and Dulaglutide, P3YELAN maintains a higher GLP-1R agonist activity in a long time.

Example 4. Random Blood Glucose Testing after Dosing in db/db Mice

Hypoglycemic experiments in leptin receptor-deficient type II diabetes (db/db) mice were carried out. The db/db mice were screened and grouped evenly according to three indicators: bod weight, non-fasting blood glucose, and OGTT response before drug administration. Each group consists of 6 mice, individuals that are too large or too small were excluded, and the non-fasting blood glucose should be greater than 15 mM. P3YELAN was dissolved in 50 mM phosphate buffer (pH 7.4), 5% sorbitol and 0.02% v/v Tween-80. Dulaglutide or P3YELAN was injected subcutaneously (multiple dosings). The dosage of Dulaglutide was 10 nmol/kg/4d, and P3YELAN was given at low (1 nmol/kg/d), medium (3 nmol/kg/d), and high dosages (6 nmol/kg/d). On day 0 to day 4, random blood glucose was monitored in all animals every day, and then detected once every 4 days, with the measurement dates arranged on day 6, 10, 14, 18, 22, 26, 30, 34.

Figure 6:
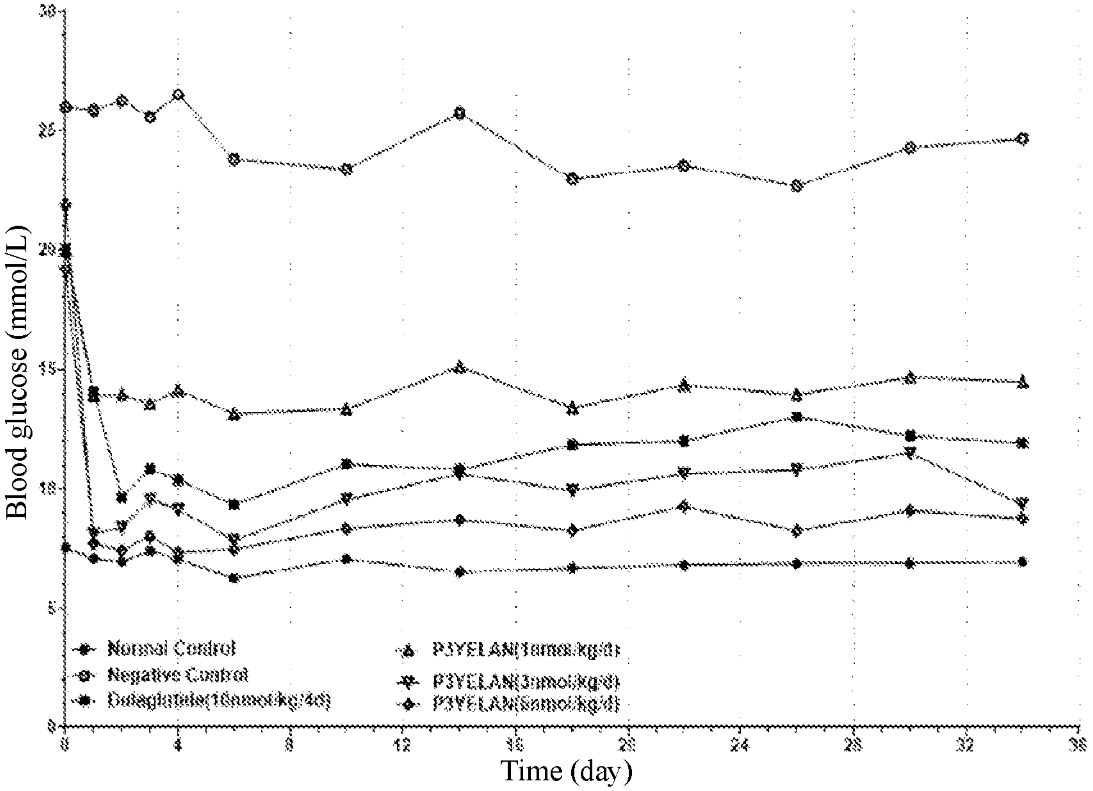
FIG. 6 shows the random blood glucose changing results after administration of the incretin analogue P3YELAN in db/db mice; Dulaglutide was taken as the positive control; normal animals without diseases as the normal control; a solvent control (not giving P3YELAN or the positive control drug) as the negative control.

The changing trend of blood glucose was shown in FIG. 6. The results showed that, at a dosage of 3 nmol/kg/d or 6 nmol/kg/d, the blood glucose level in test animals who have been given P3YELAN was much lower than that in those given Dulaglutide (10 nmol/kg/4d).

Example 5. Weight Loss Experiments in Diet-Induced Obesity (DIO) Mice

Preparation of DIO mouse models: About 7-week-old male C57BL/6J male mice were fed with high-fat diet (60% kcal from fat) for another 16 weeks (totally 23 weeks), and the test was conducted when the body weight reached about 45 g. DIO mice were randomly grouped, with 6 mice in each group and no difference in basal body weight, and weighed every day. P3YELAN, Liraglutide or PBS was injected subcutaneously. The dosage of Liraglutide was 40 nmol/kg/d, and the glucagon derivative was given at low (5 nmol/kg/d) and high dosages (20 nmol/kg/d). Measurement of body weight was started on the first dosing day, and continued until the end of the experiment Day 30. The food intake and weight were recorded every day and kept consistent. After the completion of the experiment, the blood lipids and fasting blood glucose were detected. Fasting on the evening of Day 28, and measuring the fasting blood glucose on Day 29.

Figure 7:
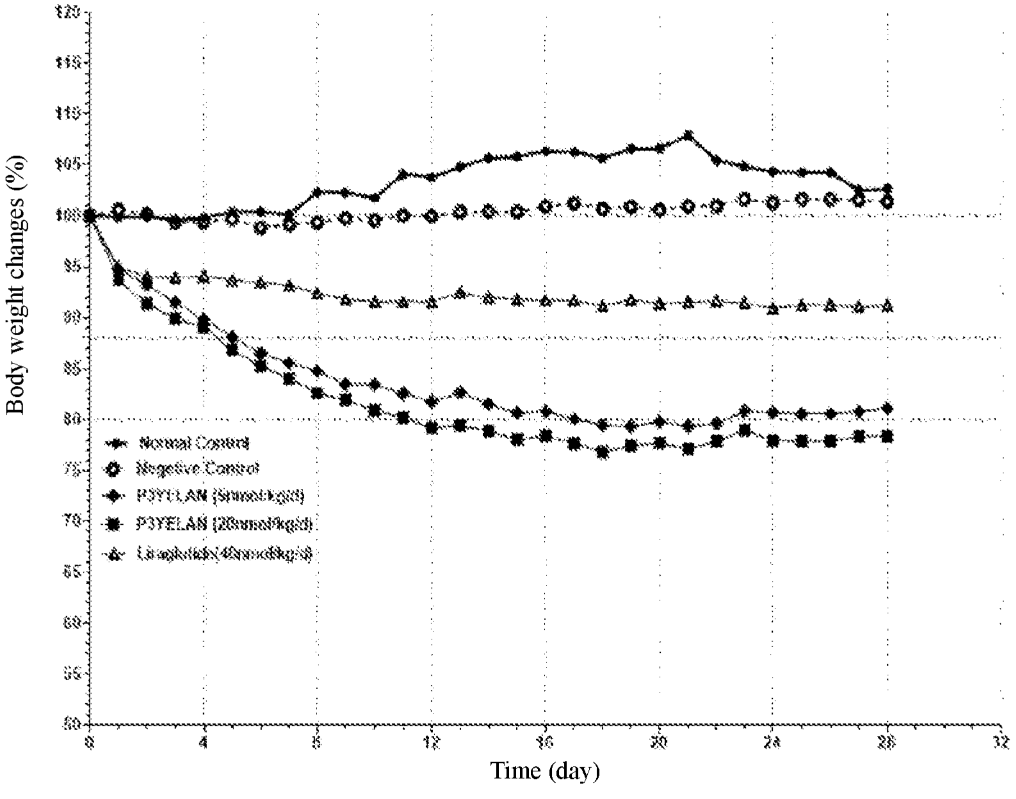
FIG. 7 shows the body weight changing results after administration of the incretin analogue P3YELAN in DIO mice; Liraglutide was taken as the positive control; normal animals without induced obesity as the normal control; a solvent control (not giving P3YELAN or the positive control drug) as the negative control.
Figure 8:
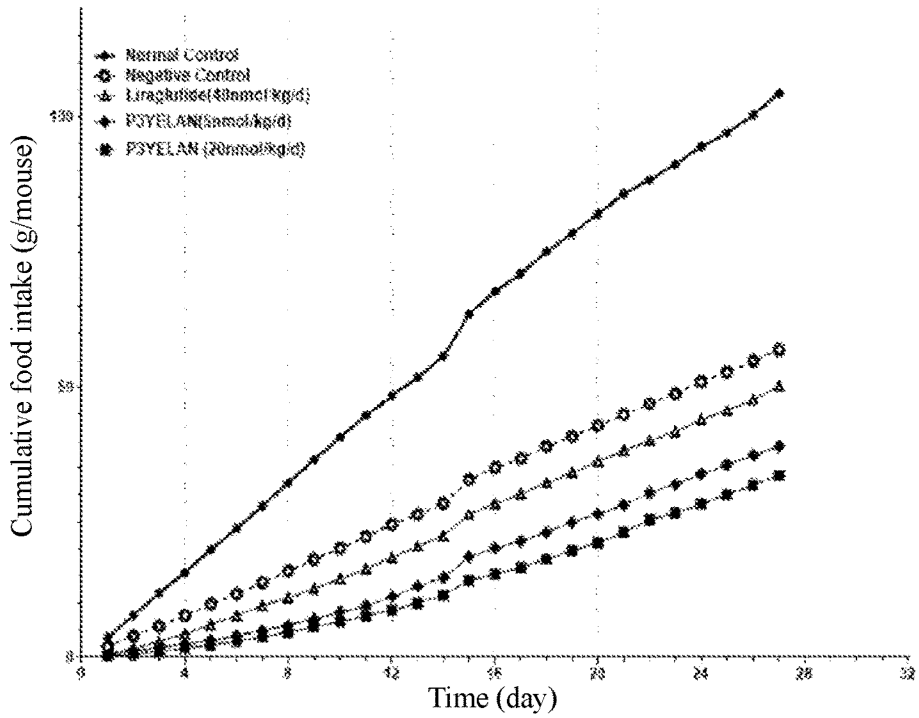
FIG. 8 shows the cumulative food intake changing results after administration of the incretin analogue P3YELAN in DIO mice; Liraglutide was taken as the positive control; normal animals without induced obesity as the normal control; a solvent control (not giving P3YELAN or the positive control drug) as the negative control.

The assay results of body weight changes of test animals were shown in FIG. 7, showing that P3YELAN in two dosage groups all could significantly reduce the body weight of the test animals, whose effect of reducing body weight was better than that of Liraglutide. The assay results of food intake of test animals were shown in FIG. 8, showing that P3YELAN in two dosage groups all could significantly reduce the food intake of the test animals, whose effect of reducing food intake was better than that of Liraglutide.

Figure 9:
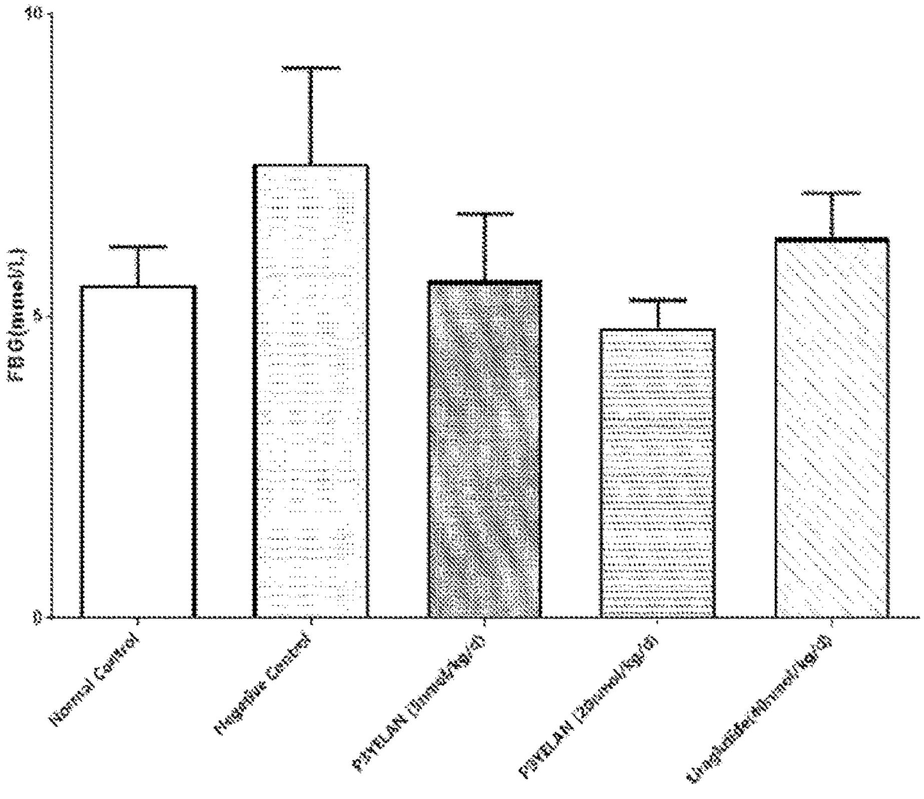
FIG. 9 shows the fasting blood glucose detection results after administration of the incretin analogue P3YELAN in DIO mice; Liraglutide was taken as the positive control; normal animals without induced obesity as the normal control; a solvent control (not giving P3YELAN or the positive control drug) as the negative control.

The assay results of fasting blood glucose of test animals were shown in FIG. 9, showing that P3YELAN in two dosage groups all could significantly reduce the fasting blood glucose of the test animals, whose effect of reducing fasting blood glucose was better than that of Liraglutide.

In summary, the P3YELAN peptide of the present disclosure effectively overcomes some technical defects in the prior art and has good industrial utilization value.

The above examples are only illustrative of the principles and effects of the present disclosure, but are not intended to limit the present disclosure. Anyone skilled in the art can modify or change the above examples without departing from the spirit and scope of the present disclosure. Therefore, all equivalent modifications or changes made by those with ordinary knowledge in the technical field without departing from the spirit and technical idea disclosed in the present disclosure shall still be encompassed by the claims of the present disclosure.

What is claimed is:

1. An incretin analogue, comprising a glucagon-like polypeptide and a long-chain fatty acid linked to the glucagon-like polypeptide; wherein an amino acid sequence of the glucagon-like polypeptide is shown in Formula (I):

(I)

(SEQ ID NO: 2)
YSEGTFTSD$X_{10}$SKYLDSQAAQDFVQWLLAGGPSSGAPPPS;

wherein $X_{10}$ of the amino acid sequence of SEQ ID NO: 2 is an amino acid lysine (K), C-terminus of the amino acid sequence of SEQ ID NO: 2 is OH or $NH_2$;

wherein the long-chain fatty acid is linked to $X_{10}$ of the amino acid sequence of SEQ ID NO: 2.

2. The incretin analogue according to claim 1, wherein the long-chain fatty acid is a fatty acid containing 14 to 20 carbons.

3. The incretin analogue according to claim 1, wherein the glucagon-like polypeptide is linked to the long-chain fatty acid via a linker.

4. A method for activating human glucagon-like peptide-1 receptors, glucose-dependent insulinotropic polypeptide receptors and/or glucagon receptors, or for alleviating or treating metabolic diseases, comprising administering the incretin analogue according to claim 1 to a subject in need thereof.

5. The method according to claim 4, wherein the metabolic diseases comprise: hyperglycemia-associated metabolic diseases or hyperlipemia-associated metabolic diseases;

the hyperglycemia-associated metabolic diseases comprise: diabetes or diabetes-associated metabolic syndromes; wherein the diabetes-associated metabolic syndromes comprise insulin resistance and glucose intolerance; or the hyperlipemia-associated metabolic diseases comprise: obesity, hyperlipemia, fatty liver, hypertriglyceridemia, hypercholesteremia, low HDL cholesterol, high LDL cholesterol; wherein the fatty liver comprises nonalcoholic fatty liver disease or comprises nonalcoholic steatohepatitis.

6. A composition, comprising the incretin analogue according to claim 1, and a carrier; wherein the composition is a pharmaceutical, food, or nutraceutical.

7. A glucagon-like polypeptide, wherein an amino acid sequence of the glucagon-like polypeptide is shown in Formula (I):

(SEQ ID NO: 2)
YSEGTFTSD$X_{10}$SKYLDSQAAQDFVQWLLAGGPSSGAPPPS (I);

wherein $X_{10}$ of the amino acid sequence of SEQ ID NO: 2 is an amino acid lysine (K), C-terminus of the amino acid sequence of SEQ ID NO: 2 is OH or $NH_2$.

8. A method for preparing the incretin analogue of claim 1, comprising: linking the glucagon-like polypeptide to the long-chain fatty acid;

wherein the long-chain fatty acid is linked to $X_{10}$ of the amino acid sequence of SEQ ID NO: 2.

9. A method for reducing food intake, reducing fat, reducing body weight or lowering blood glucose, comprising administering the incretin analogue according to claim 1 to a subject in need thereof.

10. A pillbox, comprising:

the incretin analogue according to claim 1.

11. A method for reducing food intake, reducing fat, reducing body weight or lowering blood glucose, comprising administering the composition according to claim 6 to a subject in need thereof.

12. A pillbox, comprising the composition according to claim 6.

13. The incretin analogue according to claim 2, wherein the long-chain fatty acid is a fatty acid containing 16 to 18 carbons.

14. The incretin analogue according to claim 2, wherein the long-chain fatty acid is a linear saturated monocarboxylic acid.

15. The incretin analogue according to claim 2, wherein the long-chain fatty acid is palmitic acid.

16. The incretin analogue according to claim 1, wherein the C-terminus of SEQ ID NO: 2 is $NH_2$.

17. The incretin analogue according to claim 3, wherein the linker reacts with $X_{10}$ of the amino acid sequence of SEQ ID NO: 2 and reacts with active groups of the long-chain fatty acid.

18. The incretin analogue according to claim 3, wherein the linker comprises at least 1 unit of -gamma-glutamyl-.

19. The incretin analogue according to claim 3, wherein the linker is -gamma-glutamyl-(OEG)n-, wherein n=0, 1, or 2, and OEG is-2-(2-(2-aminoethoxy)ethoxy)acetyl-.

20. The incretin analogue according to claim 1, wherein the incretin analogue is shown in Formula (II):

(II)
(SEQ ID NO: 6)
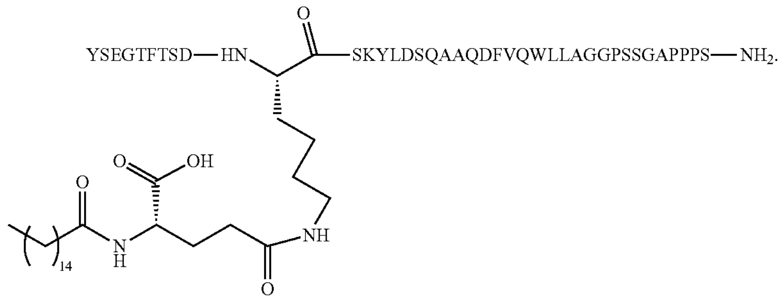
* * * * *